(12) United States Patent
Zdeblick et al.

(10) Patent No.: US 8,712,549 B2
(45) Date of Patent: Apr. 29, 2014

(54) METHOD AND SYSTEM FOR MONITORING AND TREATING HEMODYNAMIC PARAMETERS

(75) Inventors: Mark Zdeblick, Portola Valley, CA (US); George M. Savage, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 1874 days.

(21) Appl. No.: 10/734,490

(22) Filed: Dec. 11, 2003

(65) Prior Publication Data

US 2004/0193021 A1    Sep. 30, 2004

Related U.S. Application Data

(60) Provisional application No. 60/432,929, filed on Dec. 11, 2002.

(51) Int. Cl.
*A61N 1/00* (2006.01)
(52) U.S. Cl.
USPC .............................................. 607/122; 606/1
(58) Field of Classification Search
USPC ......... 600/300, 325, 327, 332, 341, 486, 490, 600/372, 373; 607/116, 122
See application file for complete search history.

(56) References Cited

U.S. PATENT DOCUMENTS

| | | |
|---|---|---|
| 2,956,586 A | 10/1960 | Zeigler et al. |
| 3,888,260 A | 6/1975 | Fischell |
| 3,985,123 A | 10/1976 | Herzlinger et al. |
| 4,164,946 A | 8/1979 | Langer |
| 4,262,982 A | 4/1981 | Kenny |
| 4,397,314 A | 8/1983 | Vaguine |
| 4,399,820 A | 8/1983 | Wirtzfeld et al. |

(Continued)

FOREIGN PATENT DOCUMENTS

| | | |
|---|---|---|
| EP | 0659388 | 6/1995 |
| EP | 0 659 388 | 8/1995 |

(Continued)

OTHER PUBLICATIONS

Kovacs, "Technology Development for a Chronic Neutral Interface", A dissertation, Stanford University (Aug. 1990), pp. 9, 225-234, 257, 276.

(Continued)

*Primary Examiner* — Navin Natnithithadha
*Assistant Examiner* — Etsub Berhanu
(74) *Attorney, Agent, or Firm* — Bozicevic, Field & Francis LLP; Bret E. Field

(57) ABSTRACT

A multiplexed medical carrier provides for sensing one or more patient parameters and/or delivering energy via separately identifiable effectors. The carrier includes a body and at least two electrical conductors coupled with at least two effectors. Effectors may be any combination of sensors, actuators or both. Sensors may measure such parameters as pressure, oxygen content, volume, conductivity, fluid flow rate, or any other chemical or physical parameters. Actuators may be used, for example, to pace a heart, stimulate muscle or neural tissue, broadcast ultrasonic energy, emit light, heat or other forms of radiation, or deliver any form of energy or substance. A method for collecting medical data from a patient includes interrogating a network of multiplexed sensors residing on parallel conductors in the patient, including addressing a first addressable sensor in the network to obtain data and addressing a second addressable sensor in the network to obtain data.

3 Claims, 9 Drawing Sheets

(56) References Cited

U.S. PATENT DOCUMENTS

| | | | |
|---|---|---|---|
| 4,600,454 A | 7/1986 | Plummer | |
| 4,603,705 A | 8/1986 | Speicher et al. | |
| 4,628,934 A | 12/1986 | Pohndorf et al. | |
| 4,628,935 A | 12/1986 | Jones et al. | |
| 4,750,494 A | 6/1988 | King | |
| 4,776,334 A | 10/1988 | Prionas | |
| 4,815,472 A | 3/1989 | Wise et al. | |
| 4,877,032 A | 10/1989 | Heinze et al. | |
| 4,878,898 A | 11/1989 | Griffin et al. | |
| 4,881,410 A | 11/1989 | Wise et al. | |
| 4,902,273 A | 2/1990 | Choy et al. | |
| 5,004,275 A | 4/1991 | Miller | |
| 5,005,613 A | 4/1991 | Stanley | |
| 5,035,246 A | 7/1991 | Heuvelmans et al. | |
| 5,072,737 A | 12/1991 | Goulding | |
| 5,111,816 A | 5/1992 | Pless et al. | |
| 5,113,868 A | 5/1992 | Wise et al. | |
| 5,119,852 A | 6/1992 | Von Benda | |
| 5,156,151 A * | 10/1992 | Imran | 600/375 |
| 5,156,154 A | 10/1992 | Valenta, Jr. et al. | |
| 5,158,536 A | 10/1992 | Sekins et al. | |
| 5,176,619 A | 1/1993 | Segalowitz | |
| 5,188,106 A | 2/1993 | Nappholz et al. | |
| 5,209,238 A * | 5/1993 | Sundhar | 600/551 |
| 5,213,098 A | 5/1993 | Bennett et al. | |
| 5,243,981 A | 9/1993 | Hudrlik | |
| 5,285,744 A | 2/1994 | Grantham et al. | |
| 5,305,745 A | 4/1994 | Zacouto et al. | |
| 5,313,020 A * | 5/1994 | Sackett | 174/113 C |
| 5,318,591 A | 6/1994 | Causey, III et al. | |
| 5,391,199 A | 2/1995 | Ben-Haim | |
| 5,411,532 A | 5/1995 | Mortazavi | |
| 5,411,537 A | 5/1995 | Munshi et al. | |
| 5,417,717 A | 5/1995 | Salo et al. | |
| 5,419,767 A | 5/1995 | Eggers et al. | |
| 5,423,323 A | 6/1995 | Orth | |
| 5,433,198 A | 7/1995 | Desai | |
| 5,476,485 A | 12/1995 | Weinberg et al. | |
| 5,487,752 A | 1/1996 | Salo et al. | |
| 5,490,323 A | 2/1996 | Thacker et al. | |
| 5,509,411 A | 4/1996 | Littmann et al. | |
| 5,535,752 A | 7/1996 | Halperin et al. | |
| 5,544,656 A | 8/1996 | Pitsillides et al. | |
| 5,549,650 A | 8/1996 | Bornzin et al. | |
| 5,563,762 A | 10/1996 | Leung et al. | |
| 5,579,234 A | 11/1996 | Wiley et al. | |
| 5,579,764 A | 12/1996 | Goldreyer | |
| 5,591,142 A | 1/1997 | Van Erp | |
| 5,593,430 A | 1/1997 | Renger | |
| 5,628,777 A | 5/1997 | Moberg et al. | |
| 5,643,330 A | 7/1997 | Holsheimer et al. | |
| 5,662,587 A | 9/1997 | Grundfest et al. | |
| 5,674,258 A | 10/1997 | Henschel et al. | |
| 5,676,153 A | 10/1997 | Smith et al. | |
| 5,683,429 A | 11/1997 | Mehra | |
| 5,713,937 A | 2/1998 | Nappholz et al. | |
| 5,720,768 A | 2/1998 | Verboven-Nelissen | |
| 5,743,267 A | 4/1998 | Nikolic et al. | |
| 5,751,050 A | 5/1998 | Ishikawa et al. | |
| 5,755,759 A | 5/1998 | Cogan | |
| 5,788,647 A | 8/1998 | Eggers | |
| 5,797,903 A * | 8/1998 | Swanson et al. | 606/34 |
| 5,800,460 A | 9/1998 | Powers et al. | |
| 5,800,465 A | 9/1998 | Thompson et al. | |
| 5,810,735 A | 9/1998 | Halperin et al. | |
| 5,814,089 A | 9/1998 | Stokes et al. | |
| 5,836,987 A | 11/1998 | Baumann et al. | |
| 5,843,148 A * | 12/1998 | Gijsbers et al. | 607/116 |
| 5,860,964 A | 1/1999 | Willekens et al. | |
| 5,873,849 A | 2/1999 | Bernard | |
| 5,895,416 A | 4/1999 | Barreras, Sr. et al. | |
| 5,902,234 A | 5/1999 | Webb | |
| 5,902,248 A | 5/1999 | Millar et al. | |
| 5,913,814 A | 6/1999 | Zantos | |
| 5,924,997 A | 7/1999 | Campbell | |
| 5,935,084 A | 8/1999 | Southworth | |
| 5,938,690 A | 8/1999 | Law et al. | |
| 5,941,904 A | 8/1999 | Johnston et al. | |
| 5,957,957 A | 9/1999 | Sheldon | |
| 5,991,661 A | 11/1999 | Park et al. | |
| 5,999,848 A | 12/1999 | Gord et al. | |
| 5,999,849 A | 12/1999 | Gord et al. | |
| 6,002,963 A | 12/1999 | Mouchawar et al. | |
| 6,004,269 A | 12/1999 | Crowley et al. | |
| 6,009,349 A | 12/1999 | Mouchawar et al. | |
| 6,015,386 A | 1/2000 | Kensey et al. | |
| 6,024,704 A | 2/2000 | Meador et al. | |
| 6,032,699 A | 3/2000 | Cochran et al. | |
| 6,033,398 A | 3/2000 | Farley et al. | |
| 6,038,480 A * | 3/2000 | Hrdlicka et al. | 607/116 |
| 6,044,297 A | 3/2000 | Sheldon et al. | |
| 6,044,299 A | 3/2000 | Nilsson | |
| 6,052,624 A | 4/2000 | Mann | |
| 6,058,329 A | 5/2000 | Salo et al. | |
| 6,061,593 A | 5/2000 | Fischell et al. | |
| 6,077,136 A | 6/2000 | Arai et al. | |
| 6,078,830 A | 6/2000 | Levin et al. | |
| 6,081,748 A | 6/2000 | Struble et al. | |
| 6,083,216 A | 7/2000 | Fischer et al. | |
| 6,115,626 A * | 9/2000 | Whayne et al. | 600/427 |
| 6,115,636 A | 9/2000 | Ryan | |
| 6,120,442 A | 9/2000 | Hickey | |
| 6,141,588 A | 10/2000 | Cox et al. | |
| 6,141,593 A | 10/2000 | Patag | |
| 6,155,267 A | 12/2000 | Nelson | |
| 6,163,716 A * | 12/2000 | Edwards et al. | 600/374 |
| 6,163,725 A | 12/2000 | Peckham et al. | |
| 6,165,135 A | 12/2000 | Neff | |
| 6,171,252 B1 | 1/2001 | Roberts | |
| 6,197,021 B1 | 3/2001 | Panescu et al. | |
| 6,197,677 B1 | 3/2001 | Lee et al. | |
| 6,206,835 B1 | 3/2001 | Spillman, Jr. et al. | |
| 6,206,874 B1 | 3/2001 | Ubby et al. | |
| 6,214,032 B1 | 4/2001 | Loeb et al. | |
| 6,223,080 B1 | 4/2001 | Thompson | |
| 6,234,973 B1 | 5/2001 | Meador et al. | |
| 6,253,109 B1 * | 6/2001 | Gielen | 607/45 |
| 6,264,606 B1 | 7/2001 | Ekwall et al. | |
| 6,277,078 B1 | 8/2001 | Porat et al. | |
| 6,287,256 B1 | 9/2001 | Park et al. | |
| 6,289,250 B1 | 9/2001 | Tsuboi et al. | |
| 6,299,582 B1 | 10/2001 | Brockway et al. | |
| 6,301,500 B1 | 10/2001 | Van Herk et al. | |
| 6,309,350 B1 | 10/2001 | Van Tassel et al. | |
| 6,309,385 B1 | 10/2001 | Simpson | |
| 6,328,699 B1 | 12/2001 | Eigler et al. | |
| 6,360,123 B1 | 3/2002 | Kimchi et al. | |
| 6,363,279 B1 | 3/2002 | Ben-Haim et al. | |
| 6,366,811 B1 | 4/2002 | Carlson | |
| 6,370,431 B1 | 4/2002 | Stoop et al. | |
| 6,406,677 B1 | 6/2002 | Carter et al. | |
| 6,418,348 B1 | 7/2002 | Witte | |
| 6,421,567 B1 | 7/2002 | Witte | |
| 6,438,408 B1 | 8/2002 | Mulligan et al. | |
| 6,466,820 B1 | 10/2002 | Juran et al. | |
| 6,473,638 B2 | 10/2002 | Ferek-Petric | |
| 6,473,653 B1 * | 10/2002 | Schallhorn et al. | 607/116 |
| 6,477,395 B2 | 11/2002 | Schulman et al. | |
| 6,477,417 B1 | 11/2002 | Levine | |
| 6,484,057 B2 | 11/2002 | Ideker et al. | |
| 6,484,727 B1 | 11/2002 | Vaska et al. | |
| 6,496,730 B1 | 12/2002 | Kleckner et al. | |
| 6,580,946 B2 | 6/2003 | Struble | |
| 6,584,362 B1 | 6/2003 | Scheiner et al. | |
| 6,600,954 B2 | 7/2003 | Cohen et al. | |
| 6,611,714 B1 | 8/2003 | Mo | |
| 6,625,493 B2 | 9/2003 | Kroll et al. | |
| 6,628,989 B1 | 9/2003 | Penner et al. | |
| 6,643,546 B2 | 11/2003 | Mathis et al. | |
| 6,666,826 B2 | 12/2003 | Salo et al. | |
| 6,728,562 B1 | 4/2004 | Budd et al. | |
| 6,812,796 B2 | 11/2004 | Pryanishnikov et al. | |
| 6,885,889 B2 | 4/2005 | Chinchoy | |
| 6,934,584 B1 | 8/2005 | Wong et al. | |

(56) References Cited

U.S. PATENT DOCUMENTS

| | | |
|---|---|---|
| 6,957,107 B2 | 10/2005 | Rogers et al. |
| 6,978,184 B1 | 12/2005 | Marcus et al. |
| 6,993,384 B2 | 1/2006 | Bradley et al. |
| 6,994,676 B2 | 2/2006 | Mulligan et al. |
| 7,047,084 B2 | 5/2006 | Erickson et al. |
| 7,174,218 B1 | 2/2007 | Kuzma |
| 7,200,437 B1 | 4/2007 | Nabutovsky et al. |
| 7,200,439 B2 | 4/2007 | Zdeblick et al. |
| 7,204,798 B2 | 4/2007 | Zdeblick et al. |
| 7,214,189 B2 | 5/2007 | Zdeblick et al. |
| 7,267,649 B2 | 9/2007 | Zdeblick et al. |
| 7,270,669 B1 | 9/2007 | Sra |
| 7,294,334 B1 | 11/2007 | Michal et al. |
| 7,467,016 B2 | 12/2008 | Colborn |
| 7,892,675 B1 | 2/2011 | Tsukamoto |
| 2001/0000187 A1 | 4/2001 | Peckham et al. |
| 2001/0002924 A1 | 6/2001 | Tajima |
| 2001/0025192 A1 | 9/2001 | Gerber et al. |
| 2001/0047138 A1 | 11/2001 | Kokate et al. |
| 2001/0053882 A1 | 12/2001 | Haddock et al. |
| 2002/0026183 A1 | 2/2002 | Simpson |
| 2002/0040236 A1 | 4/2002 | Lau et al. |
| 2002/0045921 A1 | 4/2002 | Wolinsky et al. |
| 2002/0077568 A1 | 6/2002 | Haddock |
| 2002/0077673 A1 | 6/2002 | Penner et al. |
| 2002/0095196 A1 | 7/2002 | Linberg |
| 2002/0099419 A1 | 7/2002 | Cohen et al. |
| 2002/0099430 A1 | 7/2002 | Verness |
| 2002/0111560 A1 | 8/2002 | Kokate et al. |
| 2002/0120186 A1 | 8/2002 | Keimel |
| 2002/0151816 A1 | 10/2002 | Rich et al. |
| 2002/0156417 A1 | 10/2002 | Rich et al. |
| 2002/0161307 A1 | 10/2002 | Yu et al. |
| 2002/0169445 A1 | 11/2002 | Jain et al. |
| 2002/0193859 A1 | 12/2002 | Schulman et al. |
| 2003/0036773 A1 | 2/2003 | Whitehurst et al. |
| 2003/0045920 A1 | 3/2003 | Belden et al. |
| 2003/0065364 A1 | 4/2003 | Wellman et al. |
| 2003/0078623 A1 | 4/2003 | Weinberg et al. |
| 2003/0105496 A1 | 6/2003 | Yu et al. |
| 2003/0135248 A1 | 7/2003 | Stypulkowski |
| 2003/0153952 A1 | 8/2003 | Auricchio et al. |
| 2003/0191502 A1 | 10/2003 | Sharma et al. |
| 2003/0204233 A1 | 10/2003 | Laske et al. |
| 2003/0216800 A1 | 11/2003 | Ebert et al. |
| 2004/0000713 A1 | 1/2004 | Yamashita et al. |
| 2004/0024440 A1 | 2/2004 | Cole |
| 2004/0034394 A1 | 2/2004 | Woods et al. |
| 2004/0039417 A1 | 2/2004 | Soykan et al. |
| 2004/0044368 A1 | 3/2004 | Prinzen et al. |
| 2004/0093053 A1 | 5/2004 | Gerber et al. |
| 2004/0097965 A1 | 5/2004 | Gardeski et al. |
| 2004/0098074 A1 | 5/2004 | Erickson et al. |
| 2004/0143154 A1 | 7/2004 | Lau et al. |
| 2004/0161528 A1 | 8/2004 | Martinez et al. |
| 2004/0183209 A1 | 9/2004 | Lin |
| 2004/0193021 A1 | 9/2004 | Zdeblick et al. |
| 2004/0199235 A1 | 10/2004 | Younis |
| 2004/0215049 A1 | 10/2004 | Zdeblick et al. |
| 2004/0220637 A1 | 11/2004 | Zdeblick et al. |
| 2004/0254483 A1 | 12/2004 | Zdeblick et al. |
| 2004/0260346 A1 | 12/2004 | Overall et al. |
| 2005/0027320 A1 | 2/2005 | Nehls et al. |
| 2005/0054892 A1 | 3/2005 | Lau et al. |
| 2005/0075677 A1 | 4/2005 | Ganion et al. |
| 2005/0075683 A1 | 4/2005 | Miesel et al. |
| 2005/0102011 A1 | 5/2005 | Lau et al. |
| 2005/0246004 A1 | 11/2005 | Cameron et al. |
| 2005/0267542 A1 | 12/2005 | David et al. |
| 2006/0035147 A1 | 2/2006 | Lam et al. |
| 2006/0058588 A1 | 3/2006 | Zdeblick |
| 2006/0122678 A1 | 6/2006 | Olsen et al. |
| 2006/0161211 A1 | 7/2006 | Thompson et al. |
| 2006/0170486 A1 | 8/2006 | Tranchina et al. |
| 2006/0247539 A1 | 11/2006 | Schugt et al. |
| 2006/0264775 A1 | 11/2006 | Mills et al. |
| 2006/0265038 A1 | 11/2006 | Hagen et al. |
| 2007/0100399 A1 | 5/2007 | Parramon et al. |
| 2007/0123944 A1 | 5/2007 | Zdeblick |
| 2007/0135721 A1 | 6/2007 | Zdeblick |
| 2007/0173896 A1 | 7/2007 | Zdeblick |
| 2007/0179569 A1 | 8/2007 | Zdeblick |
| 2007/0198066 A1 | 8/2007 | Greenberg et al. |
| 2007/0203517 A1 | 8/2007 | Williams et al. |
| 2007/0203537 A1 | 8/2007 | Goetz et al. |
| 2007/0219591 A1 | 9/2007 | Zdeblick et al. |
| 2007/0219608 A1 | 9/2007 | Swoyer et al. |
| 2007/0255336 A1 | 11/2007 | Herbert et al. |
| 2007/0255373 A1 | 11/2007 | Metzler et al. |
| 2007/0255460 A1 | 11/2007 | Lopata |
| 2008/0007186 A1 | 1/2008 | Lu et al. |
| 2008/0021292 A1 | 1/2008 | Stypulkowski |
| 2008/0027289 A1 | 1/2008 | Zdeblick |
| 2008/0039916 A1 | 2/2008 | Colliou et al. |
| 2008/0045826 A1 | 2/2008 | Greenberg et al. |
| 2008/0058656 A1 | 3/2008 | Costello et al. |
| 2008/0061630 A1 | 3/2008 | Andreu et al. |
| 2008/0091246 A1 | 4/2008 | Carey et al. |
| 2008/0097227 A1 | 4/2008 | Zdeblick et al. |
| 2008/0097566 A1 | 4/2008 | Colliou |
| 2008/0114230 A1 | 5/2008 | Addis |
| 2008/0140141 A1 | 6/2008 | Ben-David et al. |
| 2008/0140162 A1 | 6/2008 | Goetz et al. |
| 2008/0140167 A1 | 6/2008 | Hagen et al. |
| 2008/0147168 A1 | 6/2008 | Ransbury et al. |
| 2008/0167702 A1 | 7/2008 | Ransbury et al. |
| 2008/0177343 A1 | 7/2008 | Dal Molin et al. |
| 2008/0200802 A1 | 8/2008 | Bhavaraju et al. |
| 2008/0234588 A1 | 9/2008 | Feldman et al. |
| 2008/0255647 A1 | 10/2008 | Jensen et al. |
| 2008/0294062 A1 | 11/2008 | Rapoport et al. |
| 2008/0294218 A1 | 11/2008 | Savage et al. |
| 2008/0306394 A1 | 12/2008 | Zdeblick et al. |
| 2009/0024184 A1 | 1/2009 | Sun et al. |
| 2009/0054946 A1 | 2/2009 | Sommer et al. |
| 2009/0054947 A1 | 2/2009 | Bourn et al. |
| 2009/0088811 A1 | 4/2009 | Wulfman |
| 2009/0149902 A1 | 6/2009 | Kumar et al. |
| 2009/0299447 A1 | 12/2009 | Jensen et al. |
| 2010/0030294 A1 | 2/2010 | Wong et al. |
| 2010/0204766 A1 | 8/2010 | Zdeblick et al. |
| 2011/0208067 A1 | 8/2011 | Edman et al. |
| 2011/0224578 A1 | 9/2011 | Edman et al. |

FOREIGN PATENT DOCUMENTS

| | | |
|---|---|---|
| EP | 1048321 | 11/2000 |
| EP | 1050265 | 11/2000 |
| EP | 1 138 033 | 9/2001 |
| EP | 1136033 | 9/2001 |
| EP | 1266606 | 12/2002 |
| EP | 1426079 | 6/2004 |
| EP | 1938861 | 7/2008 |
| FR | 2097337 | 2/1972 |
| JP | 6456031 | 2/1988 |
| JP | 2099036 | 4/1990 |
| JP | 3-055032 | 3/1991 |
| JP | 5269136 | 10/1993 |
| JP | 6501177 | 2/1994 |
| JP | 6-506619 | 4/1994 |
| JP | 7-542 | 1/1995 |
| JP | 2000139833 | 5/2000 |
| JP | 2000350705 | 12/2000 |
| JP | 2002272758 | 9/2002 |
| WO | WO9912607 | 3/1999 |
| WO | WO9913561 | 3/1999 |
| WO | WO9913574 | 3/1999 |
| WO | WO9952588 | 10/1999 |
| WO | WO0009206 | 2/2000 |
| WO | WO0143821 | 6/2001 |

(56) References Cited

FOREIGN PATENT DOCUMENTS

| | | |
|---|---|---|
| WO | 0195787 | 12/2001 |
| WO | WO02053228 | 7/2002 |
| WO | WO 02/065894 A2 | 8/2002 |
| WO | WO2004020040 | 3/2004 |
| WO | WO 2004/052182 A2 | 6/2004 |
| WO | WO 2004/052182 A3 | 6/2004 |
| WO | WO 2004/066814 A2 | 8/2004 |
| WO | WO 2004/066814 A3 | 8/2004 |
| WO | WO 2004/066817 A2 | 8/2004 |
| WO | WO 2004/066817 A3 | 8/2004 |
| WO | WO 2004/067081 A2 | 8/2004 |
| WO | WO 2004/067081 A3 | 8/2004 |
| WO | WO2004066825 | 8/2004 |
| WO | WO2005118064 | 12/2005 |
| WO | WO2006029090 | 3/2006 |
| WO | WO2006042039 | 4/2006 |
| WO | WO2006069322 | 6/2006 |
| WO | WO2006069323 | 6/2006 |
| WO | WO2006073915 | 7/2006 |
| WO | WO2006105474 | 10/2006 |
| WO | WO2007005641 | 1/2007 |
| WO | WO2007075974 | 7/2007 |
| WO | WO2007120884 | 10/2007 |
| WO | WO2007149546 | 12/2007 |
| WO | WO2008004010 | 1/2008 |
| WO | WO2008008755 | 1/2008 |
| WO | WO2008027639 | 3/2008 |
| WO | WO2009029894 | 3/2009 |

OTHER PUBLICATIONS

Receveur et al., "Latterally Moving Bi-Stable MEMS DC-Switch for Biomedical Applications," Medtronic Bakken Research Center, The Netherlands (2004), pp. 864-856.

Auricchio et al., "The Pacing Therapies for Congestive Heart Failure (PATH-CHF) Study: Rationale, Design, and Endpoints of a Prospective Randomized Multicenter Study," Am J Cardiol, 1999; 83:130D-135D.

Borky, J.M. and Wise, K.D., "Integrated Signal Conditioning for Silicon Pressure Sensors" *IEEE Transactions on Electron Devices*, vol. ED-28, No. 12 (Dec. 1979) pp. 1908-1910.

Little et al, "The Output of the Heart and its Control" Physiology of the Heart and Circulation, 4th ed. 1989 Year Book Medical Publishers Inc. pp. 165-187.

Meisel et al., "Transvenous Biventricular Defibrillation", The American Journal of Cardiology, vol. 86 (9A), Nov. 2000 pp. 76K-85K.

Paolocci et al., "Positive inotropic and lusitropic effects of HNO/NO in failing hearts: Independence from β-adrenergic signaling" PNAS vol. 100, No. 9 (2003) 5537-5542.

U.S. Appl. No. 11/917,992, filed Jul. 13, 2009 (Specification, Claims, Abstract and Figures as filed); Jensen et al., (2009) "Deployable Epicardial Electrode and Sensor Array" 69pp.

U.S. Appl. No. 12/097,959, filed Nov. 17, 2008 (Specification, Claims, Abstract and Figures as filed); Zdeblick et al., (2008) "Implantable Integrated Circuit" 199pp.

U.S. Appl. No. 12/395,538, filed Feb. 27, 2009 (Specification, Claims, Abstract and Figures as filed); Bi et al., (2009) "Integrated Circuit Implementation and Fault Control System, Device, and Method" 163pp.

\* cited by examiner

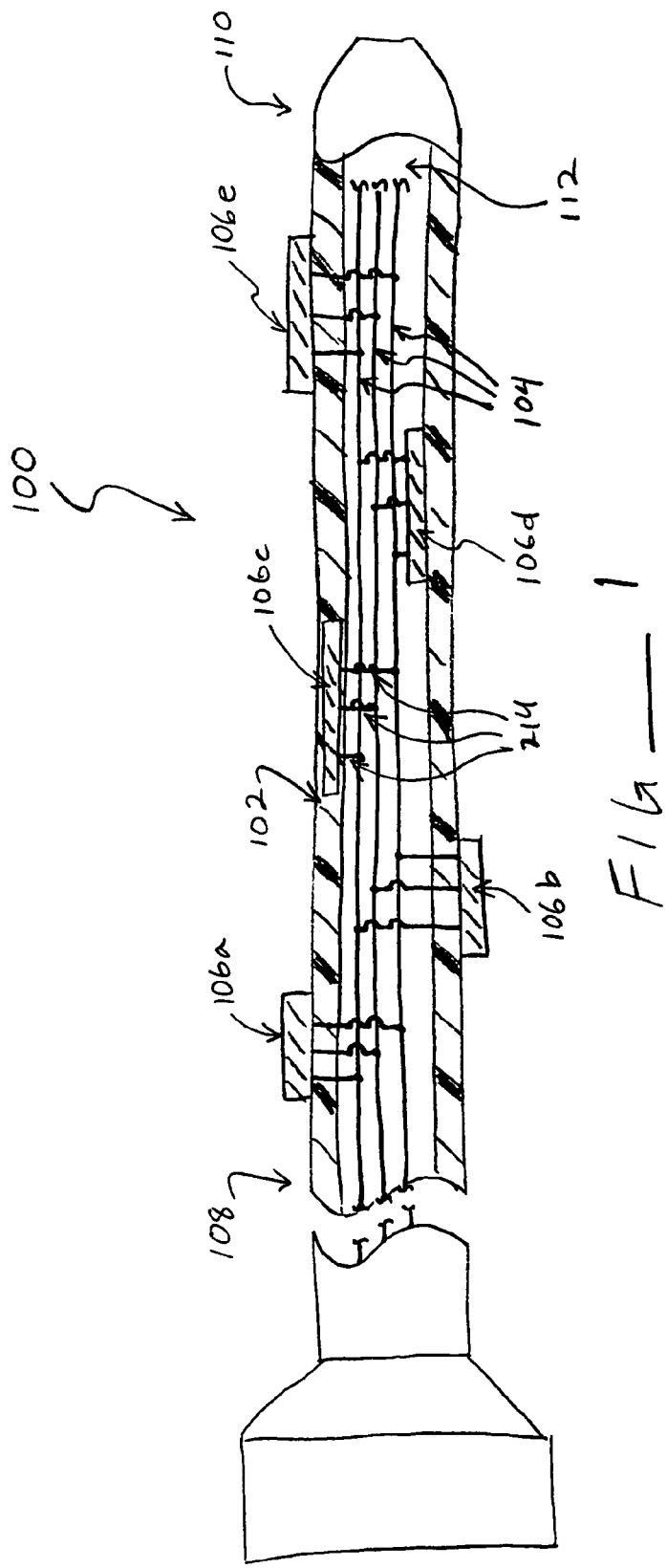

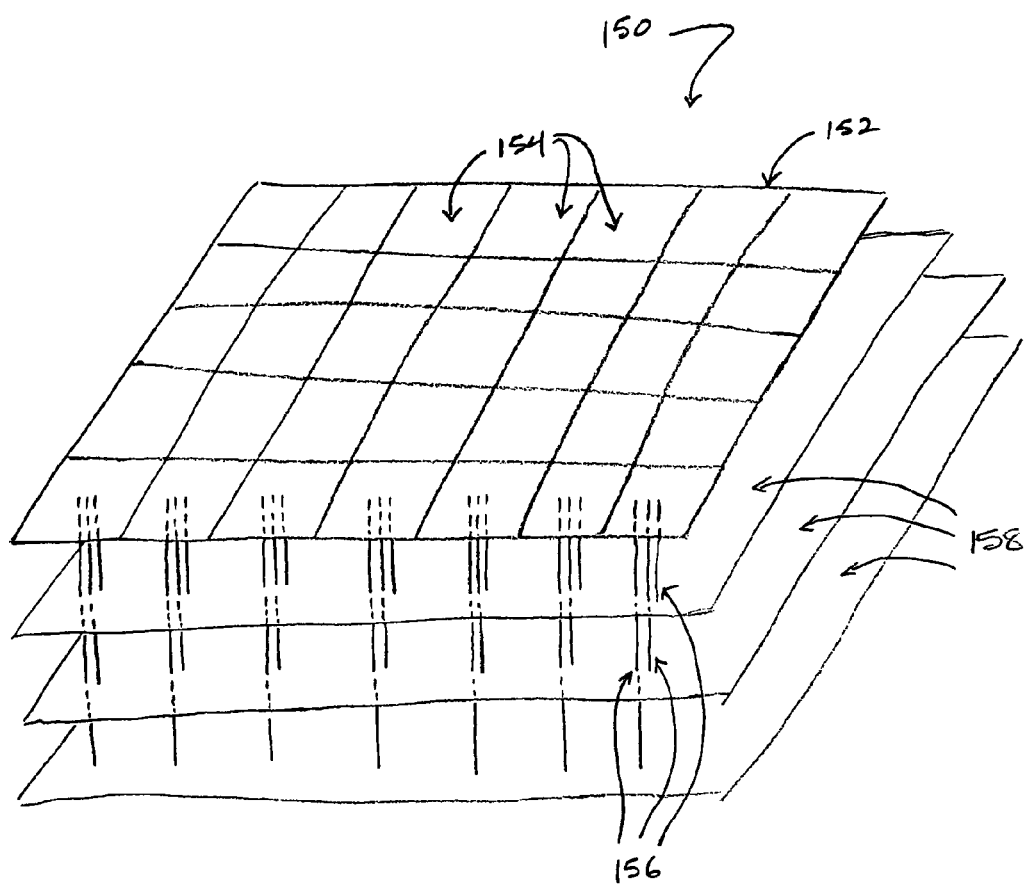
FIG___ 1A

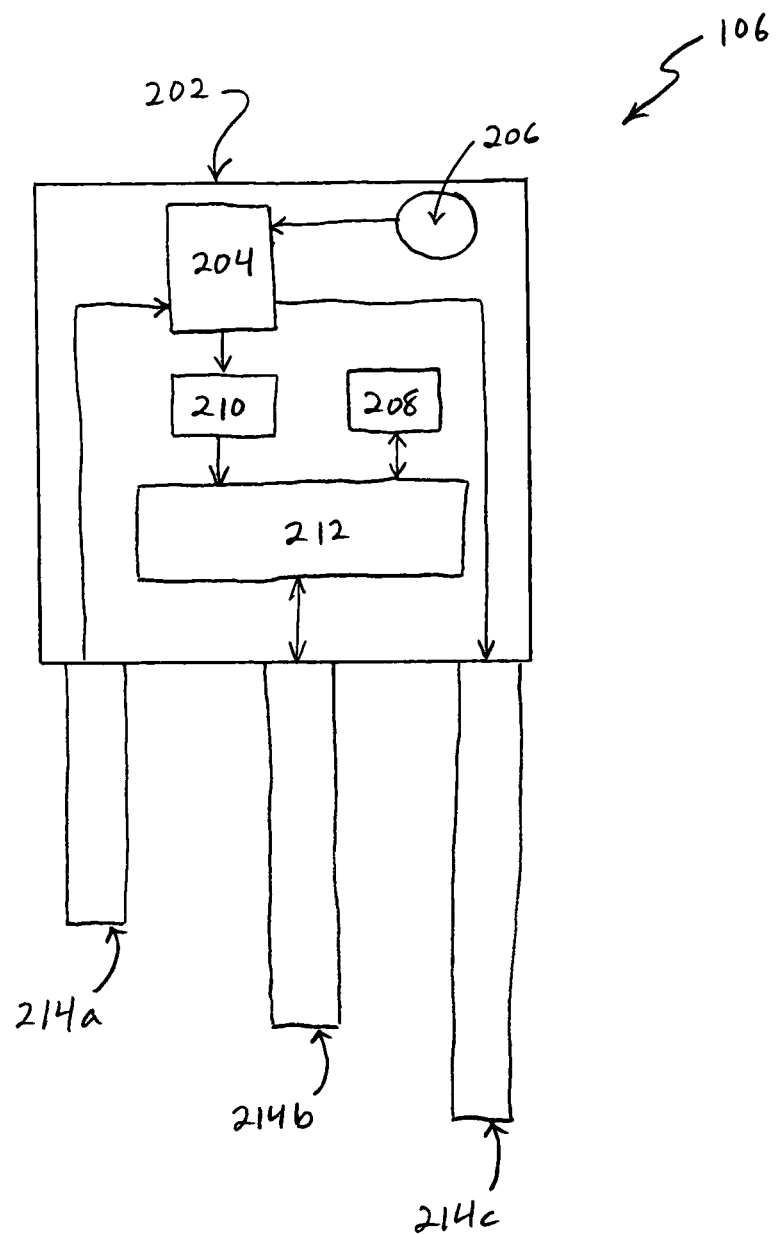
FIG_2

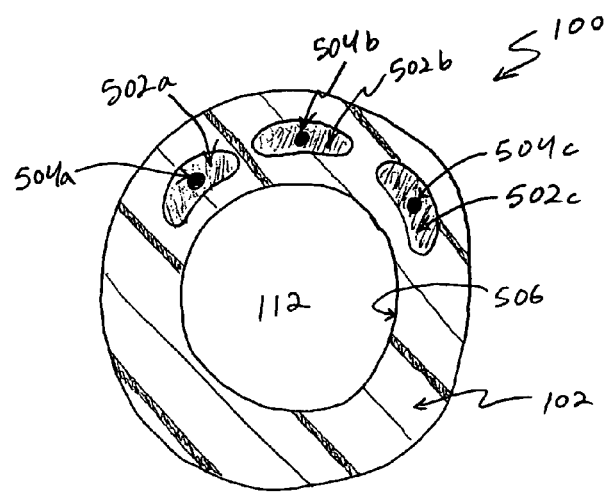
FIG_5
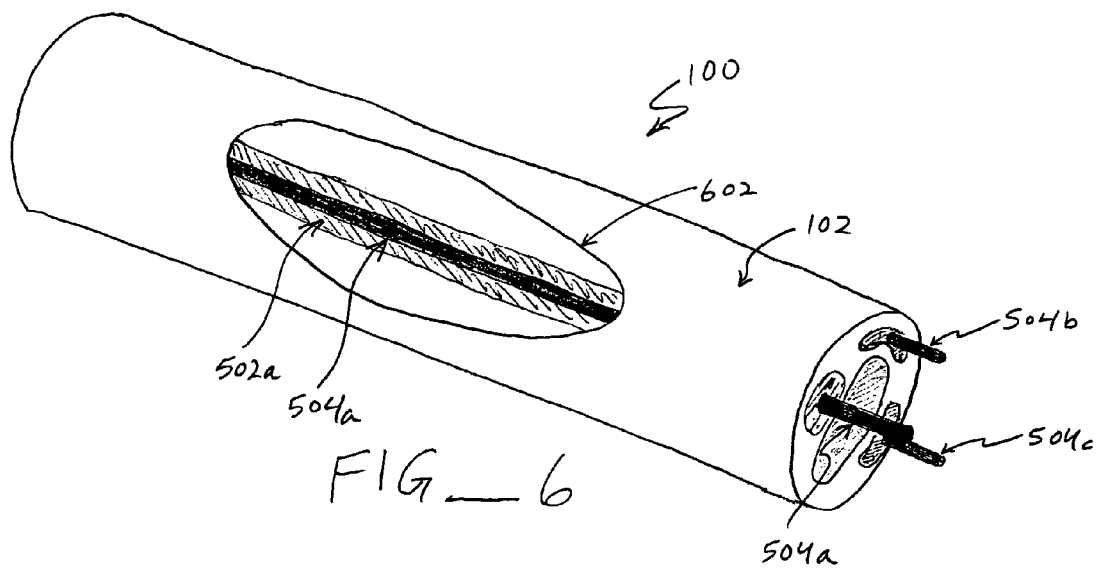
FIG_6

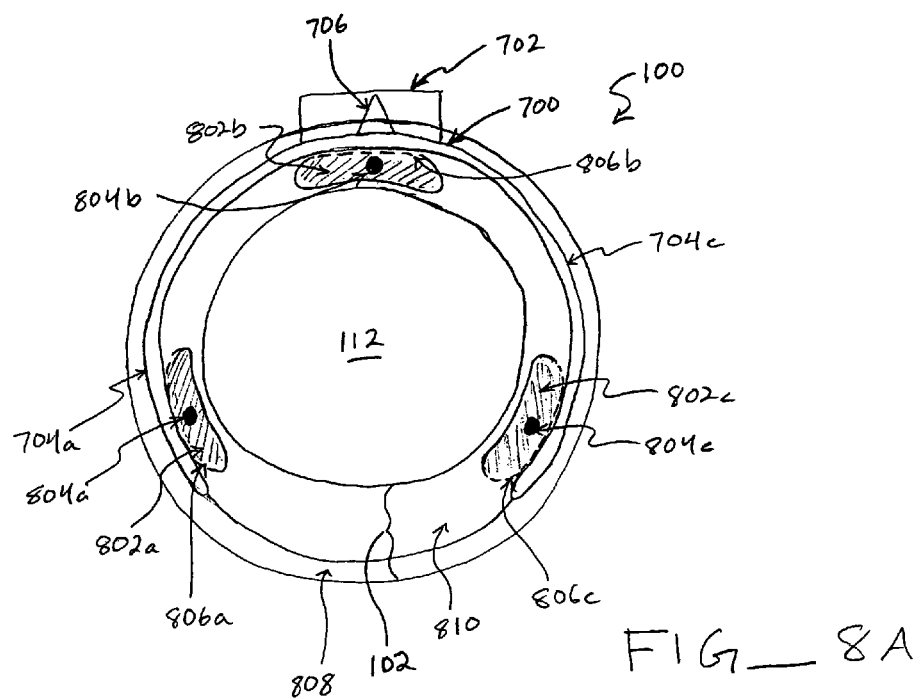
FIG__8A
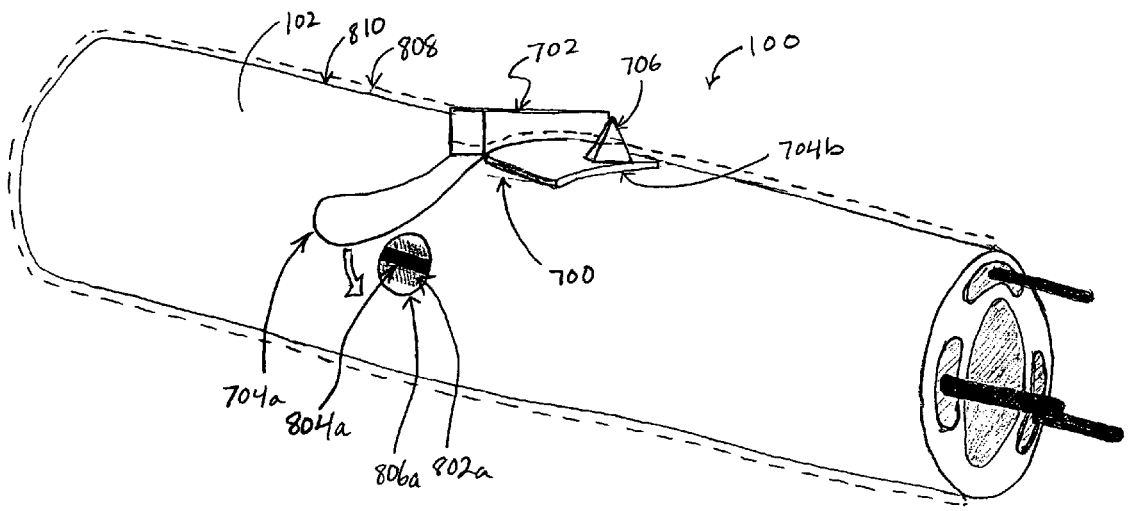
FIG__8B

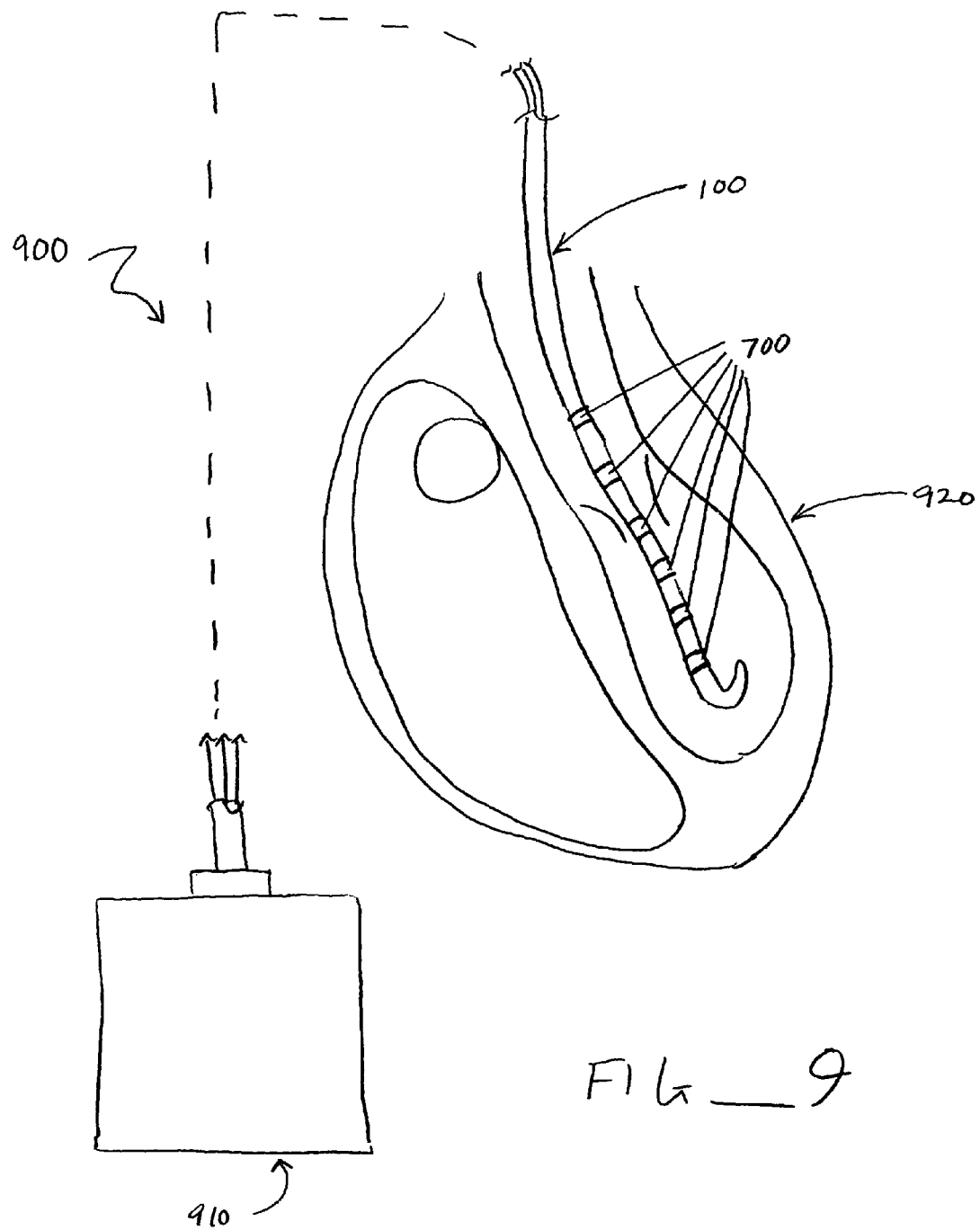
FIG_9

METHOD AND SYSTEM FOR MONITORING AND TREATING HEMODYNAMIC PARAMETERS

CROSS REFERENCE TO RELATED APPLICATIONS

This application claims priority to U.S. Provisional Patent Application No. 60/432,929, filed on Dec. 11, 2002, which is hereby fully incorporated by reference. This application is related to U.S. Provisional Patent Application No. 60/529,325, entitled "Cardiovascular Pressure Sensor Devices and Methods," filed concurrently with this application, which is hereby fully incorporated by reference.

BACKGROUND OF THE INVENTION

1. Field of the Invention

The present invention relates generally to medical devices and methods. More particularly, the present invention relates to medical devices that carry multiplexed effectors for performing a variety of diagnostic and therapeutic procedures.

Intravascular and intraluminal interventions and monitoring have become essential in modern cardiology and other medical fields. Of particular interest to the present invention, a variety of intravascular catheters, implantable sensors, implantable stimulation leads, and other devices have been developed for monitoring and affecting cardiac performance and other patient parameters. While enjoying significant utility, such monitoring and therapeutic catheters have generally included only a single or limited number of sensors and/or actuators (together referred to generally herein as "effectors"). Thus, the ability to monitor or affect multiple parameters and/or a single parameter at a number of distributed positions along the catheter or other device has been significantly limited. One of the main reasons why catheters and other devices have only included a limited number of effectors has been the requirement to "hard wire" each effector to a dedicated connection or other terminal on the catheter.

Therefore, it would be desirable to provide improved catheters, implantable stimulation leads, and other devices for the intravascular and intraluminal monitoring of patient parameters, such as pressure, temperature, conductivity, electrical potential, blood flow, blood volume and the like. It would also be desirable to provide improved catheters and other devices for intravascular and intraluminal delivery of therapeutic interventions, such as tissue ablation and electrical stimulation for cardiac pacing and other physiologic purposes. It would be particularly desirable to provide such devices with multiple effectors (sensors and/or actuators) distributed over the product. It would be further desirable to permit a single device to include effectors of many different types and to permit communication to and from the effectors using a limited number of wires in the devices. It would be further desirable to provide convenient fabrication methods for such devices and convenient methods for using such devices in patients. At least some of these objectives will be met by the inventions described below.

2. Description of the Background Art

Catheters having multiple electrodes for cardiac mapping, ablation and/or other purposes are shown in U.S. Pat. Nos. 4,397,314; 4,603,705; 4,776,334; 4,815,472; 4,881,410; 5,113,868; 5,419,767; 5,509,411; 5,579,764; 5,591,142; 5,662,587; 5,924,997; 5,902,248; 6,033,398; 6,309,385; and published applications U.S. 2002/0156417 A1 and U.S. 2002/0026183 A1. U.S. Pat. No. 4,815,472 describes a catheter having multiple solid state sensors permanently bonded to two common leads with multiplexing capability. U.S. Pat. No. 5,579,764 describes a mapping and ablation catheter having a common bus without multiplexing. U.S. Pat. No. 2002/0156417 describes MEMS sensing modules with conditioning circuitry connected to a dual-lead bus in the catheter.

BRIEF SUMMARY OF THE INVENTION

The present invention generally provides multiplexed medical carrier devices and systems, and methods for configuring and using multiplexed carriers. By "multiplexed" or "multiplexing," it is generally meant that a carrier may carry two or more effectors which may transmit and/or receive signals to and/or from one or more "remote" devices. A remote device may be located anywhere, either on the carrier or apart from the carrier. Typically, each effector on a multiplexed carrier will be identifiable in some way by the remote device. For example, effectors may be addressable, may transmit signals on different frequencies, at different times, and/or the like. In some instances at least, addressable effectors, particularly addressable electrodes and other actuators (as defined below) are preferred where a digital or other switching circuit is provided at or on the effector to allow external digital or other controllers or circuitry to selectively power, actuate, or otherwise initiate operation of the effector and/or the like.

Generally, multiplexing may be accomplished by any of a number of different techniques. One technique, for example, may be referred to generally as "broadcasting." Broadcasting generally refers to transmitting of any kind, and those terms are often used interchangeably herein. An example of broadcasting is a radio transmitter, which broadcasts analog information in a frequency band using either Amplitude Modulation (AM) or Frequency Modulation (FM). In either case, multiple sources broadcast at different frequencies, and multiple receivers have "tuners" that allow them to filter, or reject, all frequencies except those of interest to the receiver. Then, the signal from the accepted frequency is "de-modulated" to produce the original signal. This is an example of "basic" broadcasting, where any receiver may use the information that is broadcast from any transmitter.

A second multiplexing technique may be referred to as "frequency-domain multiplexing." Examples of this technique are provided by walkie-talkies and citizen-band (CB) radios. Each CB radio has a frequency selector that allows the transmitter to select a carrier frequency for transmission, preferably one that is not being used by another CB radio. The transmitter's voice is converted by a microphone into an analog electrical signal that modulates that carrier frequency using either AM or FM modulation. The receiver, of course, must be tuned to the same carrier frequency, or channel. It then de-modulates the received carrier signal back into an analog electrical signal, which drives the speaker that allows the receiver to hear the message. A typical CB radio might have 20 "channels" or carrier frequencies to choose from. Using this system, 20 different conversations may be transmitted and received simultaneously in the same vicinity. Each radio would use its frequency band 100% of the time.

A third exemplary multiplexing technique may be referred to as "time-domain multiplexing." An everyday example of time-domain multiplexing is a polite dinner conversation. Here, each person shares the single transmission medium of sound waves with each other. Typically, people take turns using that transmission medium to broadcast information, which may be received by any other listener. Electronically, the same principle may be used, where two wires transmit electronic information between any number of transceivers. There are two common methods for allocating time: synchronous and asynchronous. In synchronous, each transmitter is allocated a certain period of time on a regular basis to transmit information. For example, a telephone might electronically convert a voice into a 20,000 numbers per second, break up those 20,000 numbers into 100 "packets" of 200 numbers each and transmit each packet in, for example, a microsecond. Thus, 100 packets, each containing 200 numbers, might be transmitted by a single transmitter per second. Since each packet needs only 1 microsecond of transmission time, each transmitter uses only 100 microseconds of transmission time per second. Thus, each transmitter uses the transmission line only 0.1% of the time. If there were 1000 transmitters sharing the same line, for example, each would be allocated 1 microsecond out of every 1000 microseconds, usually synchronized by a clock signal. Typically, each transmitter would use the same microsecond during each 1000 microsecond period.

Other multiplexing techniques involve addressing, whereby each effector has a digital address or number. For example, each broadcast from an effector includes the digital address, which is read by each receiver. If the address corresponds to a receiver's address, then that receiver accepts the information and in some cases carries out additional instructions. Returning to the telephone example, a conversation may be digitized by an analog-to digital converter, which might convert a voice into 20,000 digital numbers per second. The telephone might broadcast every 10 ms (or 100 times per second) it's own address followed by 200 numbers representing the previous 10 ms of voice information. In a modern system, it might take less than 1 microsecond to transmit the address and the 200 numbers. The receiving station would then read that address, remember the following 200 numbers and then route those numbers, preceded by the address (or number) of the destination telephone, to each of one or more destination telephones. The receiving antennae would listen on its dedicated frequency until it "hears" its address and then remembers the next 200 numbers. A Digital-to-Analog Converter then converts those numbers, over the next 10 ms, into an analog signal that is transmitted to the speaker in or connected to the telephone. Since each telephone only uses 1 microsecond (or significantly less in high performance systems) out of every 10 ms, one can see how, at least theoretically, 1000 telephones, each allocated a 1 microsecond time slot out of every 10 ms, could share a single frequency band.

Any of these techniques, or any other suitable techniques, may be used in a multiplexed carrier of the invention. In some embodiments, for example, combinations of the above described techniques may be used, such as a combination of frequency-domain and time-domain multiplexing. As is evident from the above description, identifiable effectors on a multiplexed carrier may be addressed (or addressable) or may be identifiable by some other means, without addressing.

According to one aspect of the invention, multiplexed medical carriers comprise a body having a surface and at least two lumens, and at least two electrical conductors, each conductor disposed in a separate lumen along at least a portion of the body. The body is adapted to mount and electrically couple to the electrical conductors at least two separately identifiable effectors at a plurality of distributed locations within the body or on the surface. Each conductor may be disposed in a separate lumen along any portion of the body or along the entire length of the body. In one embodiment, for example, each conductor is disposed in a separate lumen along at least a distal portion of the body. By "a separate lumen" it is meant any separate passageway. Thus, separate lumens may be formed as separately extruded lumens in some embodiments, while in others they may comprise partitioned portions of one lumen or the like.

Carriers will usually comprise a plurality of effectors mounted on the body and coupled to the conductor(s). Coupling of the effectors with the conductors may be achieved by any suitable means. In one embodiment, for example, the conductors are uninsulated along at least part of their lengths to allow for coupling with the effectors. The term "effectors" is generally used herein to refer to sensors, actuators, sensor/actuators, or any other device that may be coupled with a carrier for performing a function. In some embodiments, for example, the at least two identifiable effectors comprise a transducer and a processor (digital or analog), where the processor is identifiable and distinguishable from all other effector processors using conventional multiplexing circuitry. The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like. In some embodiments, both sensor(s) and actuator(s) may be coupled with a carrier. In one embodiment, at least some of the effectors include a transducer and an electronic conversion circuit, wherein output from the transducer is encoded using a carrier frequency and broadcast onto one of the electrical conductors, and wherein each effector utilizes a different carrier frequency. Alternatively, at least some of the effectors may include a transducer and an electronic conversion circuit, wherein output from the transducer is broadcast onto one of the electrical conductors during a specified time interval, and wherein each effector utilizes a different time interval.

In some embodiments, the carrier body will comprise three electrical conductors electrically coupled to the effectors, each conductor being isolated in at least a portion of one of the lumens of the carrier body. The three electrical conductors may include, for example, a ground conductor, a power conductor, and a data conductor. As will be described in more detail below, such a three-wire system is most useful for connecting the effectors to an external power supply as well as collecting data and/or providing instruction to transducers within the effectors and appropriately addressing the effector with the external controller. Effectors may be coupled to electrical conductors by any suitable means, but in one embodiment they are coupled to a wire in the carrier through an opening in the body of the carrier and via a conductive material, such as a conductive gel, fluid, paste, slurry, epoxy or eutectic. The conductive material may extend through part or all of a length of the carrier, and in some embodiments may act as the electrical conductors themselves. Effectors may also be mounted on the carrier body in any suitable way, such as on an external surface or an internal surface of the body.

In one preferred embodiment, the body comprises an elongated body, such as an intravascular or other intraluminal catheter, adapted to be introduced to and through a blood vessel or other body lumen. In such cases, the conductor(s) extend axially from a distal location at or near the distal tip of the elongated body to a proximal connection, typically within a proximal hub on the catheter or other elongated body. In such cases, the multiple effectors will typically be axially spaced-apart, although they may also be circumferentially spaced apart under certain circumstances. Such catheters may comprise from two effectors to 100 effectors, typically comprising from 4 effectors to 40 effectors, and more typically comprising from 4 effectors to 12 effectors. In other preferred embodiments, the body comprises a flat surface, adapted to be positioned on a tissue such as brain tissue. In such cases, the conductor(s) are disposed along one or more additional surfaces in proximity to the flat surface. The flat surface may comprise any number of effectors, but some embodiments include from 6 effectors to 1000 effectors and more preferably from 36 effectors to 100 effectors.

In another aspect, the present invention provides an improved medical carrier of the type including a plurality of actuators. The improvement comprises providing separately addressable actuators that are multiplexed by at least one common conductor in the medical carrier. In some embodiments, for example, at least some of the actuators comprise electrodes for delivering electrical energy. In other embodiments, any other suitable actuators may be used, such as the actuators described further above. Further particular features of this aspect of the present invention are set forth above with respect to the first description of the medical carrier.

In another aspect, the present invention provides an improved medical carrier of the type including a plurality of systems. The improvement comprises separately identifiable systems that are multiplexed by at least one common conductor, with each system including at least one sensor, at least one actuator, and an electronic circuit. Sensors and actuators may be any of those described above or any other suitable sensors or actuators. In one embodiment, at least one of the plurality of systems comprises an electrode sensor for measuring electrical potential and an electrode actuator for delivering electrical energy.

In a still further aspect of the present invention, a system comprises a multiplexed medical carrier having a plurality of separately identifiable effectors distributed over a surface thereof, wherein the effectors are multiplexed by at least one common connector. The system further includes a multiplexing controller adapted to connect to the effectors via the common conductor, typically arranged as a bus together with further conductors in a conventional multiplexing system. The multiplexed medical carrier may be connected to the multiplexing controller in any conventional fashion. For example, when the multiplexed medical carrier is a catheter, a hub or cable on the catheter may be removably connected to the multiplexing controller in a conventional "hard wired" configuration. Alternatively, the multiplexing controller could be adapted for a wireless connection to the multiplexed medical carrier, in which case the medical carrier would include a transceiver for such wireless communication. Still further alternatively, the system may comprise an implantable data collection and transmission unit, which connects to an implanted multiplexed medical carrier and which wirelessly communicates with the multiplexing controller.

The present invention still further provides methods for configuring a medical carrier comprising: providing a body having a surface and at least one electrical conductor; selectively mounting at least one separately identifiable effector on the surface; and electrically coupling the at least one effector to the at least one electrical conductor through a surface penetration. Typically, two or three connections would be made between the effectors and respective conductors within the body. Selectively mounting typically comprises exposing the conductor(s) through the surface and electrically coupling a lead from the each of the effectors to each conductor. Optionally, the method may further involve encapsulating at least a portion of the body and the effector(s) with an encapsulating material. Specific aspects of the body and effectors have been described in more detail above.

In another aspect, the invention provides an improved method for configuring a medical carrier of the type including a plurality of actuators. The improvement comprises providing separately identifiable actuators that are multiplexed by at least one common conductor.

In yet another aspect of the invention, an improved method for configuring a medical carrier of the type including a plurality of systems is provided. The improvement comprises providing separately identifiable systems that are multiplexed by at least one common conductor. In some embodiments, each system comprises at least one sensor, at least one actuator, and an electronic circuit.

The present invention still further provides methods for collecting medical data from a patient. A network of multiplexed sensors residing on parallel conductors residing in the patient is interrogated. In particular, interrogating comprises (a) addressing a first addressable sensor in the network to obtain first data and (b) addressing a second addressable sensor in the network to obtain second data. Interrogating according to this method may further comprise addressing third, fourth, fifth, and even additional sensors in the network to obtain additional sets of data. Usually, the methods will further comprise powering sensors within the multiplexed network of sensors via the network. Alternatively, each sensor may transmit data without interrogation. In this case, data may be encoded by processing circuitry collocated with the sensor. The encoding scheme (e.g., by frequency, duty cycle, or digitally) allows processing circuitry located outside the patient to extract the data thereby transmitted. The data collected may include any one of pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. Typical methods will be performed where the sensors are distributed and the catheter present in the vasculature and/or within a chamber of the heart. Other methods will be performed where the sensors are distributed on a flat surface and the surface is present on or near brain tissue. Still other methods will be performed where the sensors are distributed and the catheter present in the urinary tract, reproductive tract, endoscopic surgical site, abdominal cavity, gastrointestinal tract or a joint space.

In still another aspect of the invention, a method for collecting medical data from a patient involves activating a network of multiplexed sensors residing on parallel conductors in the patient such that each activated sensor transmits sensed data. The transmitted data is received and separated into multiple data streams, each data stream comprising data from one sensor. In one embodiment, each activated sensor transmits data on a different carrier frequency. Alternatively, sensors may transmit data at different time intervals or the like.

In another aspect of the invention, a method for delivering energy or one or more substances to a patient involves addressing at least a first addressable actuator in a network of actuators to cause the first actuator to deliver energy or a substance. In some embodiments, a second addressable actuator is addressed to cause the actuator to deliver energy or a substance. Optionally, third, fourth or any number of additional actuators, may be similarly addressed. Any suitable function(s) may be performed by the actuators, as described more fully above, and the actuators may reside in any suitable location in the patient.

These and other embodiments are described more fully below.

BRIEF DESCRIPTION OF THE DRAWINGS

FIG. 1 is a schematic illustration of a multiplexed medical carrier, in the form of an intraluminal catheter, constructed in accordance with the principals of the present invention.

FIG. 1A is a schematic illustration of a multiplexed medical carrier, in the form of flat surface, constructed in accordance with the principals of the present invention FIG. 2 is a schematic illustration of an effector constructed in accordance with the principals of the present invention.

FIG. 5 illustrates a cross-sectional view of the catheter of FIG. 4.

FIG. 6 is a detailed view of the section of the body of the catheter of FIG. 4 shown with an aperture preformed in its side prior to connecting an effector according to the methods of the present invention.

FIG. 8A is a cross-sectional view of the effector of FIG. 7 mounted on the catheter body of FIG. 6.

FIG. 8B is a perspective view of a portion of a multiplexed medical carrier, showing the effector of FIGS. 7 and 8A mounted on the catheter body of FIG. 6.

FIG. 9 illustrates use of the catheter of FIG. 4 in performing intracardiac monitoring according to methods of the present invention.

DETAILED DESCRIPTION OF THE INVENTION

Figure 3A:
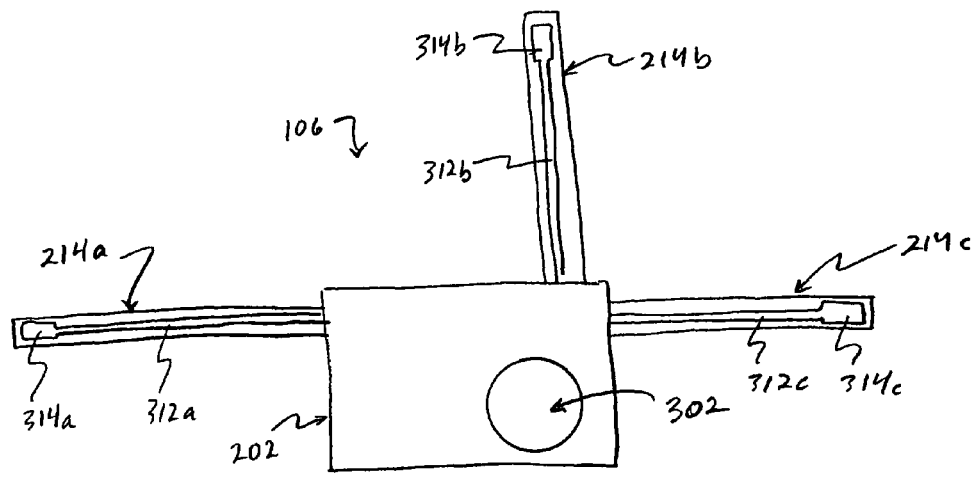
FIG. 3A illustrates a first exemplary effector for measuring pressure constructed in accordance with the principals of the present invention.

The present invention generally provides medical devices that carry multiplexed effectors for performing a variety of diagnostic and/or therapeutic procedures. Also provided are methods for making and using such devices. As described above, an "effector" on a multiplexed medical carrier may comprise a sensor, an actuator, a sensor/actuator, or any other suitable device, and any given carrier may include one or more sensors, actuators, or a combination of both. In some embodiments, a multiplexed carrier is configured as an elongate catheter, with one or more effectors disposed along its length. In other embodiments, the carrier is configured as a flat surface, with effectors disposed along the surface. Each effector is separately identifiable and all effectors on a given carrier are coupled to at least two electrical conductors disposed on, or more typically within, a body of the carrier.

The effectors may be mounted to a surface of the carrier or may be disposed within the body of the carrier. In various embodiments, such multiplexed medical carriers may be used for sensing any of a variety of data, such as pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. Alternatively, the effectors may be intended for actuation or intervention, such as providing an electrical current or voltage, setting an electrical potential, heating a substance or area, inducing a pressure change, releasing or capturing a material, emitting light, emitting sonic or ultrasound energy, emitting radiation and/or the like. Carriers may also be used in a variety of locations within a body, such as in one or more chambers of the heart, in arterial or venous vasculature, in or on brain tissue, in the urinary, gastrointestinal or reproductive tracts, in the abdominal cavity, in a joint space or the like. Methods for monitoring one or more patient parameters using a multiplexed medical carrier and for fabricating such a carrier are also provided.

With reference now to FIG. 1, a multiplexed medical carrier 100 of the present invention suitably includes a body 102, multiple electrical conductors 104 disposed in body 102, and multiple, separately identifiable effectors 106a-e, which may be disposed at distributed locations within body 102, in a lumen 112 of body 102, and/or on an exterior surface of body 102. In any given embodiment, many variations may be made in the size or configuration of body 102, in the number and type of electrical conductors 104, in the number and type of effectors 106a-e and/or the like. Thus, the embodiment shown in FIG. 1 and described further below is merely one exemplary embodiment and should not be interpreted to limit the scope of the invention as set forth in the claims.

Body 102 of multiplexed medical carrier 100 may have any suitable shape, size, configuration, dimensions and the like. In some embodiments, as in FIG. 1, body 102 comprises an elongate catheter body having a proximal end 108 and a distal end 110 and defining a central lumen 112. In addition to central lumen 112, in some embodiments body 102 includes one or more intramural lumens (not shown), which run longitudinally within body 102 and may house one or more electrical conductors 104, conductive material(s) such a gel, fluid, paste, slurry, epoxy or eutectic and/or other components of multiplexed carrier 100. (Generally, the phrase "within body 102" means within the wall of body 102. A location within central lumen 112 formed by body 102 will be referred to as "in central lumen 112.") In other embodiments, as described further below with reference to FIG. 1A, body may comprise a flat surface, with effectors being disposed along the surface and with conductors disposed along adjacent flat surfaces.

In many embodiments, body 102 may comprise a catheter body adapted for intraluminal introduction into a target body lumen or other body structure, such as vasculature or the heart. The dimensions, materials and other physical characteristics of body 102 will vary significantly depending on the body structure to be accessed and monitored. For example, one or more portions of body 102 may be flexible while one or more other portions may be relatively rigid. Body 102 may include a guidewire lumen configured for over-the-wire or rapid exchange introduction, in various embodiments. Catheter bodies intended for intravascular introduction may have a length in the range from 50 cm to 200 cm and an outer diameter in the range from 1 French to 12 French (0.33 mm:1 French). Bodies 102 will typically be composed of an organic polymer, which is fabricated by conventional extrusion techniques. Suitable polymers include polyvinylchloride, polyurethanes, polyesters, polytetrafluoroethylenes (PTFE), silicone polymers, natural rubbers, polyamides (i.e., nylons) and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques.

The resulting catheters will thus be suitable for introduction to the vascular system, the heart, or any other desired location by conventional techniques.

In embodiments in which body 102 comprises an elongated body, such as an intravascular or other intraluminal catheter, electrical conductor(s) 104 extend axially from a distal location at or near the distal tip of the elongated body to a proximal connection, typically within a proximal hub on the catheter or other elongated body 102. In such cases, effectors 106 will typically be axially spaced-apart, although they may also be circumferentially spaced apart under certain circumstances. Such catheters may comprise any suitable number of effectors, such as from two effectors 106 to 100 effectors 106, typically comprising from 4 effectors 106 to 40 effectors 106, and more typically comprising from 4 effectors 106 to 12 effectors 106.

Electrical conductors 104 generally comprise conductors running axially along all or a portion of the length of body 102. Conductors 104 may comprise thin, elongate wires, a conductive sheath or mesh disposed within or on a surface of body 102, or the like. In one embodiment, only one electrical conductor 104 is used and a conductive fluid or gel in central lumen 112 or an intramural lumen acts as a ground. More commonly, however, multiplexed medical carrier 100 includes two, or preferably three, electrical conductors 104. In some embodiments, each electrical conductor 104 is isolated at least a portion of its length. For example, in one embodiment body 102 may comprise three or more intramural lumens and each electrical conductor 104 may be housed in a separate intramural lumen. Furthermore, each electrical conductor 104 typically performs a unique function. In an embodiment having three conductors 104, for example, one conductor 104 comprises a ground conductor, one comprises a power conductor and one comprises a data conductor. A ground conductor generally acts as a conventional electrical grounding mechanism, to return electrical current to the proximal end 108 of multiplexed carrier 100. A power conductor provides energy to one or more effectors 106a-e and a data conductor may transmit data to and/or from one or more effectors 106a-e. As mentioned previously, three electrical conductors 104 is described as an exemplary embodiment only. Various other embodiments may include, one, two or more than three conductors 104. Some embodiments may even include no conductors 104, for example if wireless RF communication is used.

In a given embodiment, multiplexed medical carrier 100 may include one effector 106, two effectors, five effectors (as shown in FIG. 1) or any other suitable number of effectors 106a-e. Effectors 106a-e, which are described further below, may be of any suitable size and configuration and may be disposed within carrier body 102 (as effector 106c) on an interior surface of body 102 (as effector 106d) and/or on an exterior surface of body 102 (as effectors 106a, b and e). Furthermore, effectors 106a-e may be positioned at any suitable locations relative to the longitudinal length of body 102. For example, it may be advantageous to dispose effectors 106 along the length of carrier 100 so as to measure one or more parameters in two adjacent chambers of the heart simultaneously. Any suitable combination of numbers, types, sizes and placements of effectors 106 is contemplated within the scope of the invention.

Each effector 106a-e is coupled with each electrical conductor 104 via a lead 214. Medical carriers 100 of the present invention, such as the catheter in FIG. 1, are referred to as multiplexed carriers because multiple, separately identifiable effectors 106a-e are coupled with a single set (or "network") of electrical conductors 104. For example, in one embodiment all effectors 104 would be coupled with a common ground conductor, a common data conductor and a common power conductor. Such multiplexing provides for convenient use of multiple effectors 106 on one carrier 100, without requiring a separate set of electrical conductors 104 for each effector 104. Using separate sets of conductors for each effector 106 on the other hand, as with currently available devices, limits the number of possible effectors 106 due to constraints of size and maneuverability of the catheter.

With reference now to FIG. 1A, another embodiment of a multiplexed medical carrier 150 suitably includes a body comprising-a flat surface 152 and multiple effectors 154 disposed along surface 152. Any suitable size and configuration of surface may be used and any number of effectors may be used. In some embodiments, between 4 and 1000 effectors may be used and preferably between 36 and 100 effectors. Carrier 150 may further include one or more conductors 158, which may similarly comprise flat surfaces positioned adjacent to or in proximity with flat surface 152. One or more leads 156 may extend from each effector 154 to electronically couple with each conductor 158. In this way, each flat conductor 158 may communicate with all of the addressable effectors 154 on flat surface 152. Such a flat configuration of carrier 150 may be used for any suitable purpose, such as for placement on a bodily tissue. In one embodiment, carrier 150 is configured for placement on brain tissue.

Referring now to FIG. 2, one embodiment of an effector 106 suitably includes a chip 202, typically a silicon chip, including or coupled with one or more arms 214a -c. As will be described further below, an arm 214a -c generally comprises any suitable structure for housing an electrode, for electrically coupling effector 106 with an electrical conductor 104. Chip 202 typically includes a transducer 206, which may comprise a sensor for sensing a parameter within a vascular structure, the heart, or other body structure, or an actuator for actuating a pressure change, temperature change or any other suitable action within the body structure. Sensors may comprise any suitable sensors such as pressure sensors, volume sensors, dimension sensors, temperature or thermal sensors, oxygen or carbon dioxide sensors, electrical conductivity sensors, electrical potential sensors, pH sensors, chemical sensors, flow rate sensors, optical sensors, acoustic sensors, hematocrit sensors, viscosity sensors and the like. An actuator may perform any suitable function, such as providing an electrical current or voltage, setting an electrical potential, generating a biopotential, pacing a heart, heating a substance or area, inducing a pressure change, releasing or capturing a material, emitting light, emitting sonic or ultrasound energy, emitting radiation or the like. In some embodiments, transducer 206 may extend beyond the outer boundaries of chip 202, while in others transducer 206 may be confined wholly within chip 202. Chip also typically includes circuitry 204 for providing measurement of a parameter sensed by transducer 206.

Once a parameter is sensed by transducer 206 and processed by circuitry 204, analog data from circuitry is transferred to a processor within chip 202. Generally, a processor may include any suitable circuitry, nanotechnology apparatus or the like. In some embodiments, a processor includes an analog-to-digital (AD) converter 210 for converting data from circuitry 204 into digital data, stored address information 208 for addressing the processor, and a microprocessor 212 for receiving and processing data from the AD converter 210 and/or from data supplied by a data conductor 214b.

In some embodiments, no addressing system is used. Instead, each effector broadcasts data either during a predetermined interval or using a dedicated frequency. One embodiment may include, for example, a circuit including a voltage-controlled duty cycle oscillator that converts a differential pressure signal into an oscillator with a variable duty cycle. Such a circuit is described, for example, in U.S. Provisional Patent Application No. 60/529,325, filed concurrently with this application and previously incorporated by reference. The output of such a circuit produces a series of pulses: the ratio of the time in the "on" state to the time in the "off" state is proportional to the absolute pressure. On and off states generally represent two different voltage levels, and the off state need not be zero (0) volts. It may be preferable, in fact, to designate a positive voltage, such as 3V, as the off state and a higher voltage, such as 5V, as the on state. Any combination of voltages may be used. This series of pulses then becomes the envelope for a carrier frequency of a voltage controlled oscillator. Each of several sensors may broadcast at a different carrier frequency. An external monitor may have a number of electronic filters connected in parallel to the catheter's output line, with each filter tuned to one of the carrier frequencies. The output of each filter may, for example, comprise a series of square pulses whose duty cycle (the ratio of on time to off time) is proportional to the pressure measured by that sensor.

Circuitry, sensors, processing apparatus or any other suitable components of chip 202 may be fabricated using lithographic processes similar to those used to make transistors and micro-electromechanical systems (MEMS) devices. When a silicon chip is used, for example, a thin coating of polyimide may be spun onto a wafer and patterned. Metal lines, fabricated from a thin layer of chrome and a thicker layer of gold in one embodiment, may then be formed on the cured polyimide. A second layer of polyimide is then deposited and patterned on the wafer. During the die separation process, chip 202 remains adhered to the polyimide and the silicon is removed from under the polyimide and two or more flexible "flaps." The flexible flaps may comprise electrodes for contacting with electrical conductors 104.

Arms 214a -c may comprise any suitable means for housing electrodes or electrical leads (not shown). In fact, in some embodiments an arm 214a -c may comprise simply an electrode coupled with chip 202 via a wire or other conductive material. In some embodiments, arms 214a -c are flexible, such that they can be conformed to a surface of body 102 of a multiplexed carrier 100. Generally, any suitable arms may be used. Similarly, any number of arms 214a -c may be used, depending on the number of electrodes to be coupled with chip 202. In some embodiments, effector 106 includes three arms 104a -c, each housing one electrode corresponding to an isolated electrical conductor 104. One arm may comprise a power transmission lead 214a for transmitting energy from a power conductor 104 to circuitry 204. A second arm may comprise a data lead 214b for transmitting data between a data conductor 104 and microprocessor 212. A third arm may comprise a ground lead 214c for coupling circuitry 204 with a ground conductor 104. In other embodiments, fewer than three or more than three arms 214 may be used to couple chip 202 with one or more electrical conductors 104.

With reference now to FIG. 3A, one embodiment of an effector 106 is shown. Again, effector 106 typically includes a chip 202, coupled with one or more, and often three, flexible arms 214a -c. In one embodiment, the transducer comprises a pressure sensor 302 embedded on chip 202 for sensing pressure within a body structure, such as pressure within a blood vessel or heart chamber. In one embodiment, each arm 214 includes an electrode 314, coupled to chip 202 via a thin film wire 312. Other embodiments may alternatively include arms having electrodes 314 with other means for coupling electrodes 314 with chip 202.

Figure 3B:
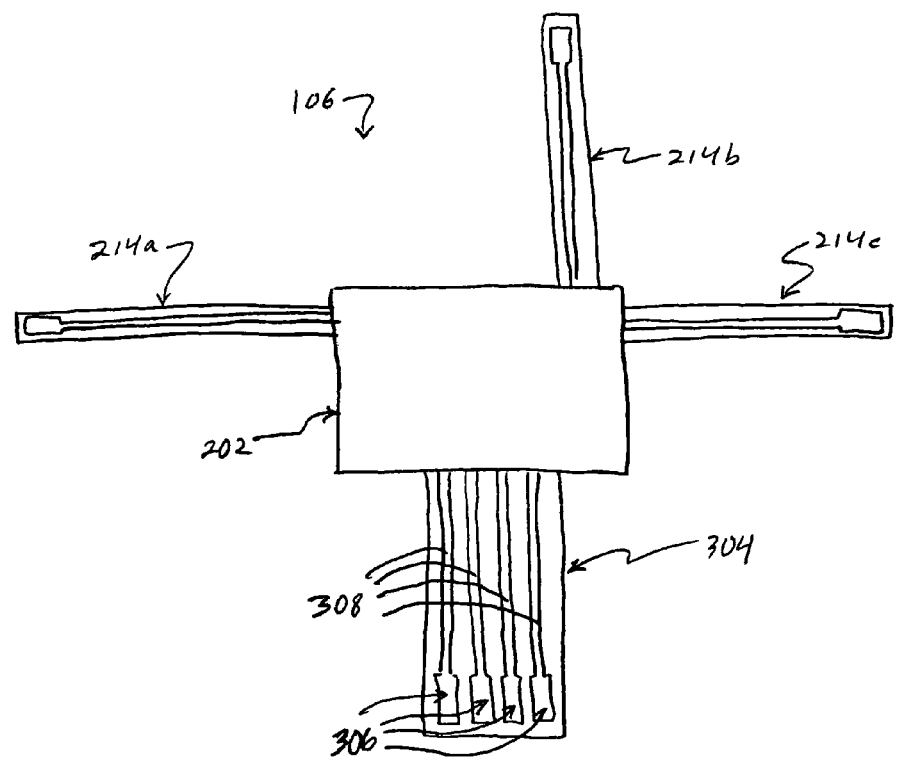
FIG. 3B illustrates a second exemplary effector for measuring electrical conductivity constructed in accordance with the principals of the present invention.

In another embodiment, and with reference to FIG. 3B, a transducer may comprise an electrical conductivity sensor 304 for sensing electrical conductivity of blood. The conductivity sensor extends beyond chip 202 to contact blood in a blood vessel, in a chamber of the heart, or in any other blood-containing body cavity. Four thin-film electrodes 306 sense electrical conductivity of the blood and are coupled with chip 202 via four flexible thin film wires 308. In other embodiments, effector 106 may be configured to sense any suitable parameter, such as but not limited to pressure, volume, dimensions, temperature, oxygen, electrical conductivity, electrical potential, pH, lactase, ejection fraction, regurgitant flow or other chemical or physical parameters and/or rates of change in any of the above parameters.

Generally, any suitable effectors, be they sensors or actuators, may be used in various embodiments of the present invention. Examples of such effectors have been described above. Some embodiments may include pressure sensor devices as described in U.S. Provisional Patent Application No. 60/529,325, filed concurrently with this application and previously incorporated by reference. Again, these or any other effectors now known or hereafter discovered may be used.

Figure 4:
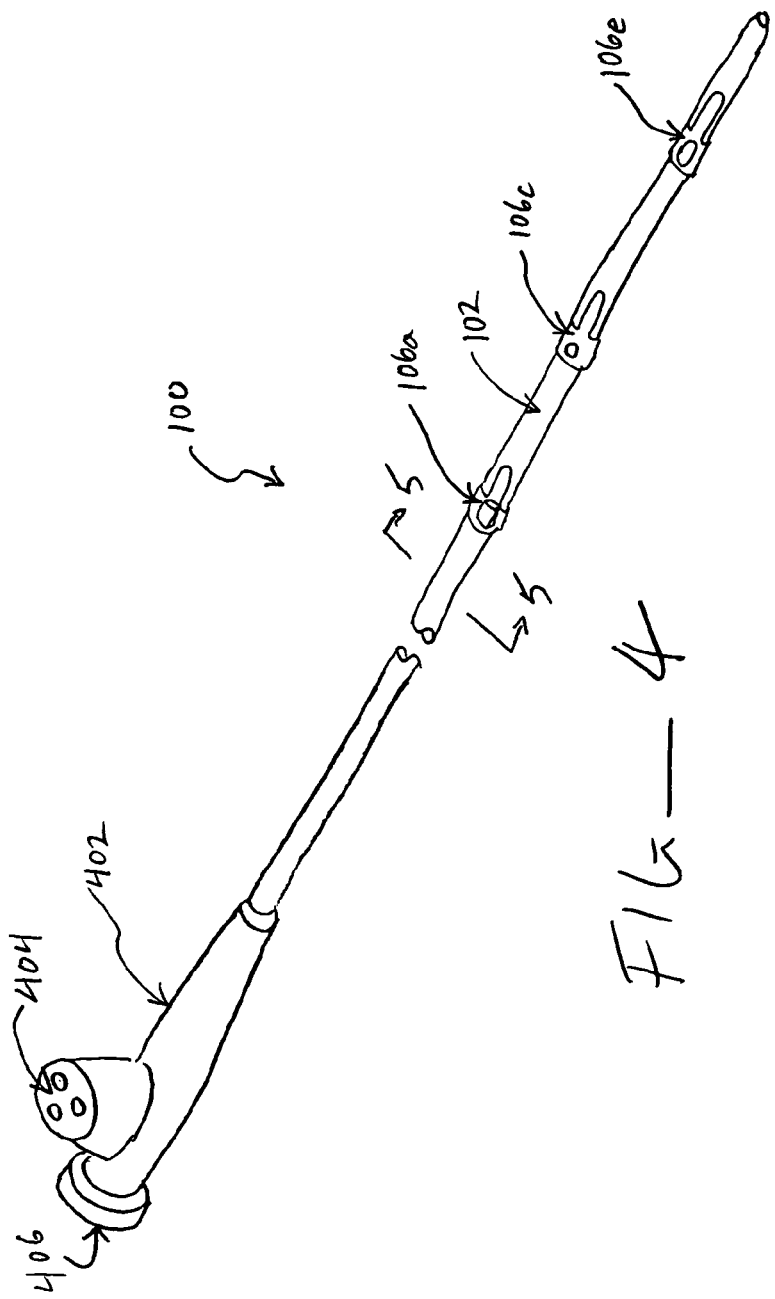
FIG. 4 is a perspective view of an intravascular or intracardiac catheter having multiple sensors thereon constructed in accordance with the principals of the present invention.

With reference now to FIG. 4, multiplexed medical carrier 100 is shown in perspective view. Carrier 100 may generally include body 102 coupled at its proximal end with a handle 402. As previously described, body 102 may include multiple effectors 106a-c disposed at dispersed locations wholly or partially on its outer surface. Handle 402 may include any suitable means for holding, manipulating, activating or otherwise using multiplexed carrier. For example, handle 402 may suitably include one or more electrical connections 404 and one or more fluidic connections.

Referring now to FIG. 5, a cross-sectional view of multiplexed medical carrier 100 is shown from the perspective demonstrated by the arrows labeled "5" in FIG. 4. In one embodiment, carrier 100 includes body 102, three separate intramural lumens 502a-c disposed within body 102, and central lumen 112, defined by body 102. Each intramural lumen 502a-c may contain an electrical conductor 504a -c. As previously discussed, each electrical conductor 504a -c may be configured to have a distinct function. For example, the three conductors in one embodiment may include a ground conductor 504a, a power conductor 504b and a data conductor 504c. In a given embodiment, fewer or additional conductors may suitably be included. Additionally, any suitable placement of conductors 504a -c within intramural lumens 502a-c is contemplated. In other embodiments, conductors 504a -c may be alternatively disposed on the inner surface 506 of central lumen 112. In still other embodiments, greater than four, five, eight or any other suitable number of intramural lumens 502a-c may be included and electrical conductors 504a -c may be disposed in adjacent or spaced-apart lumens 502. In intramural lumens 502 containing electrical conductors 504, a conductive material such as a conductive gel or fluid may be disposed within the lumen in some embodiments. Such a conductive material may act as an electrical ground, may act to couple the electrical conductor 504 with an electrode on an effector 106, or may serve any other suitable purpose. Any suitable conductive substance may be used.

In some embodiments, body 102 is fabricated from two or more layers of material. In such embodiments, intramural lumens 504a -c may be positioned between two layers of material. In one embodiment, one layer of body 102, such as a metallic mesh or solid metallic layer, comprises an electrical conductor 504 such that leads from effectors may contact that layer to achieve conductance. In some embodiments, a conducting fluid or gel may disposed in central lumen 112 and/or one or more intramural lumens 502 may act as an electrical conductor 502. Thus, it is contemplated that electrical conductors 504 may have various configurations, sizes, shapes, chemical compositions and the like.

With reference now to FIG. 6, body 102 may include one or more holes or sidewall openings 602. Sidewall openings 602 provide locations for placement of arms of effectors (not shown in FIG. 6), so that electrodes of the effectors may electrically contact electrical conductors 504. A sidewall opening 602 is generally positioned to overly a part of one or more intramural lumens 502. In FIG. 6, sidewall opening 602 overlies one intramural lumen 502a and one electrical conductor 504a. In other embodiments, opening 602 may be positioned so as to provide access to two lumens and electrical conductors, three lumens and electrical conductors, or any other suitable number. As is described further below, an arm of an effector is typically positioned over a sidewall opening 602 such that the electrode in the arm contacts conductive gel, fluid or other substance in an intramural lumen. Electrical signals may then travel through the conductive substance between the electrode of the effector and the electrical conductor in the intramural lumen 502.

Figure 7:
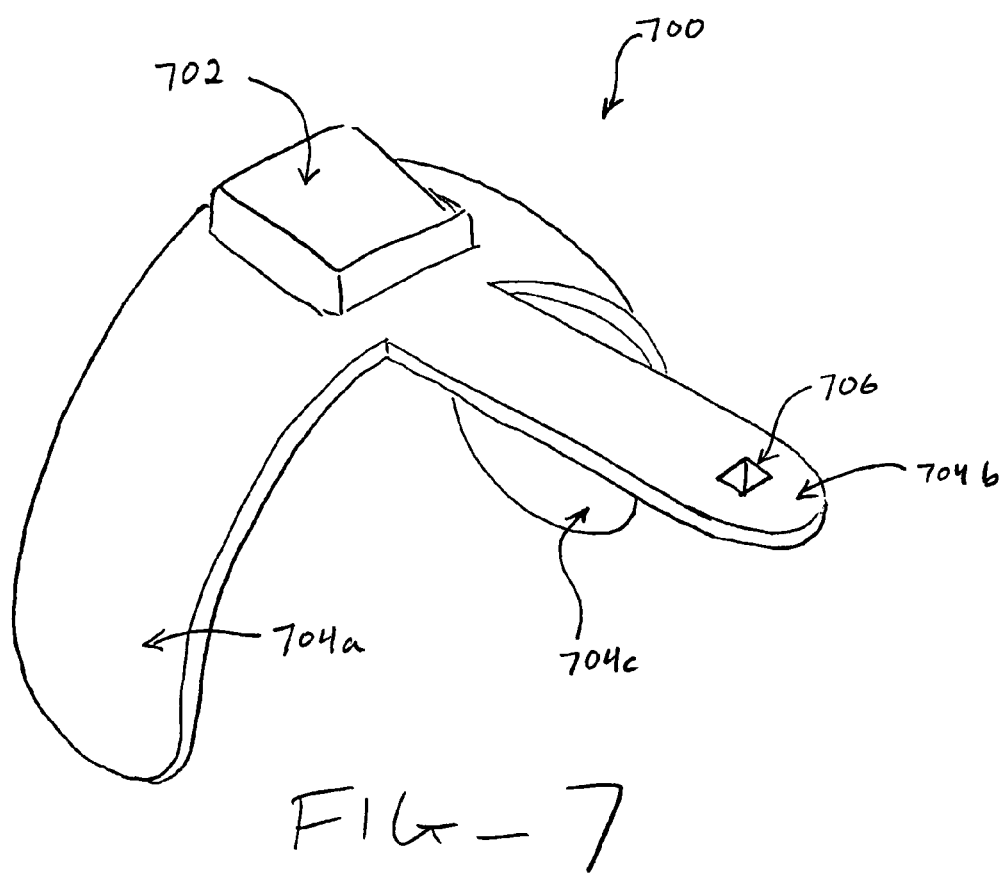
FIG. 7 illustrates an exemplary effector construction for mounting on the catheter body of FIG. 6.

With reference now to FIG. 7, one embodiment of an effector 700 includes a chip 702 and three arms 704a -c. As described above, chip 702 typically includes a transducer, such as a sensor or actuator, and an addressable processor. Arms 704a -c may extend from chip 702 in any suitable directions and may have any suitable shape, size and configuration. In one embodiment, two arms 704a and 704c are configured to wrap partially or completely around body 102 of multiplexed medical carrier 100 and a third arm 704b extends longitudinally along the outer surface of body 102. One or more arms 704 may include a protrusion 706 for extending through an outer later of body 102 to contact blood or other bodily fluid surrounding body 102. anchoring effector 700 in a location of body 102. For example, arms 704a -c may be disposed on an outer surface of body 102 and an outer cover or coating may be placed over body 102, covering leads. Protrusion 706 may extend through this outer coating or covering, sense one or more parameters and/or to actuate an effect in fluid surrounding body 102.

With reference now to FIG. 8, effector 700 may be coupled with multiplexed medical carrier 100 by any suitable means or in any configuration. In one embodiment, as shown, effector 700 may be disposed partially or wholly within body 102. For example, effector 700 may be mounted between an inner layer 810 and an outer layer 808 of body 102. In one embodiment, for example, body 102 may comprise multiple layers of extruded plastic material and effector 700 may be disposed between inner layer 810 and outer layer 808 of extruded plastic or other flexible material, such as silicone. Generally, outer layer 808 will comprise a thin layer of extruded material and may be transparent in some embodiments. Similarly, outer layer 808 may comprise a thin coating of the same material used in fabricating body 102 or of a different material. In other embodiments, effectors 700 may be glued or otherwise fastened with adhesive to an outer surface of body 102, rather than mounting effectors 700 between layers of body. In such embodiments, any suitable adhesive may be used. In some embodiments using adhesive, effectors 700 are mounted on the outer surface of body 102 in such a way that arms 704 contact body 102 and chip 202 is spaced slightly apart from the outer surface of body. In other words, chip 202 "floats" above body. Such a floating chip may confer added flexibility to carrier 100. Any other suitable means for mounting effectors 700 onto multiplexed medical catheter is contemplated. In one embodiment, for example, effectors 700 may be mounted via mechanical pressure mounting, with two or more arms of effector 700 applying force to hold effector 700 to body 102.

In embodiments in which effectors 700 are mounted between layers of body 102, one or more portions of effector 700 will typically extend through outer layer 808, such as chip 702 or anchor 706. In some embodiments, anchor 706 may also serve as a sensor or actuator and, thus, may protrude through outer layer 808 to contact blood or other substances in order to sense a parameter. All or a portion of chip 706 may also extend through outer layer 808, as desired. Other sensors, actuators, anchors or other portions of effector 700 may likewise protrude through outer layer 808 to contact blood or other substances surrounding carrier 100 or for any other purpose.

Generally, as described above, leads extend from chip 702 as part of flexible arms 704a and 704c. Arms 704 generally house an electrode coupled to chip via a flexible wire or similar electrical connection. Each electrode (not shown) is positioned by an arm 704a, 704c in proximity with an electrical conductor 804a -c. As noted above, body 102 typically includes sidewall openings 806a-c, to allow conductivity between electrodes and electrical conductors 804a -c. Conductive fluid, gel or similar substance in an intramural lumen 802a-c, comes in contact with an adjacent electrode and provides a conductive medium between the electrode and electrical conductor 804a -c.

FIG. 8B provides a perspective view of multiplexed medical carrier 100 with effector 700 as in FIG. 8A and with flexible arm 704a pulled back to show sidewall opening 806a. The dotted line represents outer layer 808, which again may comprise a thin, transparent or opaque layer or coating through which one or more portions of effector 700 protrude. Flexible arm 704a, housing one electrode, is shown pulled back to expose sidewall opening 806a in body 102. As denoted by the hollow arrow, flexible arm 704a normally lies over and completely covers opening 806a—i.e., the diameter of opening 806a is smaller than the width of the flexible arm 704a. Electrical conductor 804a is exposed in intramural lumen 802a, which contains a gel, fluid or other conductive substance. A second flexible arm 704b may be coupled with anchor 706, which protrudes through outer layer 808. In one embodiment, flexible arms are lined up to improved the die yield on a silicon wafer, so that when flattened they appear rectangular in shape.

With reference now to FIG. 9, a system 900 of the present invention may include a multiplexed medical carrier 100 and a multiplexing controller 910 adapted to connect to and control carrier 100. System 900 may be used in a variety of settings and a variety of body structures but in one embodiment is configured to measure parameters within a heart 920. In one embodiment, multiplexing controller 910 connects to multiplexing carrier 100 via a wired connection including one or more wires, cables or the like. In another embodiment, controller 910 and carrier 100 are coupled via a wireless connection. In still another embodiment, system 900 may further include an implantable data collection and transmission unit (not shown), which connects to the multiplexed carrier 100 (either via wired or wireless connection) and communicates wirelessly with multiplexing controller 910. As discussed previously, multiplexing medical carrier 100 may include any suitable number of separately addressable effectors 700 disposed at any suitable locations along carrier 100.

A method for collecting medical data from a patient according to the present invention may include interrogating a multiplexed network of sensors residing in the patient. For example, the network may include multiple effectors 700 residing in one or more chambers of a patient's heart 920. Interrogating the network may comprise addressing a first addressable sensor in the network to obtain data, addressing a second addressable sensor in the network and so on, depending on the number of addressable sensors residing in the patient. For example, third, fourth, fifth, sixth and seventh sensors could by addressed in one embodiment. Data acquired may include any of a number of parameters, such as but not limited to pressure, volume dimensions, temperature, oxygen, electrical conductivity, electrical potential, pH, lactase, ejection fraction, regurgitant flow and/or other chemical or mechanical parameters. The method may further include powering sensors within the multiplexed network of sensors via the network. One of the electrical conductors, for example, may provide power to sensors in the network. Furthermore, methods of the invention may be carried out in any suitable body structure, such as but not limited to the heart, arterial or venous vasculature, other hollow body structures such as the urinary bladder, and/or the like.

In alternative embodiments, the method may not include interrogating the multiplexed network of sensors. Instead, the sensors may be activated so as to broadcast sensed data. For example, each sensor may broadcast data using a different frequency, a different specified time span or the like. Broadcast data may then be received and processed to separate the data for the different sensors. In one embodiment, each effector relies on a single carrier frequency for its communication with the other elements or a central controller. Thus, a sensor may broadcast its data using a dedicated carrier frequency. An actuator may receive its instructions on a different dedicated frequency. In some embodiments, the effectors may communicate with one another via a network analogous to an Ethernet. For example, in one embodiment, such as when used to determine the volume of a ventricle, ultrasound broadcast transducers in electrical communication with ultrasound receivers may be placed some distance away. Distance between the transducers and the receivers may then be accurately determined from acoustic delay, even if the catheter bends. Thus, while some embodiments of multiplexing catheters employ addressing, others operate without addressing.

In one embodiment, multiplexed carrier 100 comprises a catheter, as in FIG. 9 and is used to measure pressure at multiple locations along the catheter using multiple sensor effectors 700. One sensor may be positioned near the distal tip of the catheter, such as a pigtail catheter, to measure hemodynamic parameters in a left ventricle. Another sensor could be positioned far enough away from the distal sensor so that it would be located outside the left ventricle during use. Each sensor could transmit a signal indicating pressure at the location of the sensor to an external device, such as multiplexing controller 910. The controller 910 could then subtract a downstream pressure from an upstream pressure to provide real-time measurement of the pressure gradient across the mitral valve.

In another embodiment, a multiplexed carrier 100 could be adapted to measure volume of a heart chamber, artery, other vessel or the like, using impedance plethysmography. Such a method would generally utilize two effectors 700 at spaced locations along carrier 100 which act as actuators to produce a voltage. A method might involve producing an AC current with the two effectors 700 through blood surrounding carrier 100 at a frequency of over 100 kHz, such as 125 kHz. A linear array of voltage-measuring effectors 700 would be disposed along carrier 100 between the two voltage-producing effectors 700. Electric circuits in the voltage-measuring effectors 700 would filter a time-varying potential produced by the voltage-producing effectors 700, so that only the potential variation at that frequency would be used to measure the resistance of the blood between the various voltage-measuring electrodes. If one effector 700 is also adapted to measure conductivity of the blood, then a measurement of the volume of the vessel or chamber can be inferred from the various resistance measurements.

While the above is a complete description of the preferred embodiments of the inventions, various alternatives, modifications and equivalents may be made to the described embodiments without departing from the scope of the invention as set forth in the appended claims. For example, many variations to the methods just described may be made to measure or affect different parameters, to measure or affect parameters at different locations in a body and/or the like. Thus, the above description is provided for exemplary purposes only and should not be interpreted to limit the invention as set forth in the claims.

What is claimed is:

1. A method for configuring a medical carrier having a body and at least two conductors, wherein the method comprises the steps of:
   providing separately identifiable effectors, wherein the effectors are axially spaced apart along the length of the carrier's body and wherein at least one effector comprises:
      at least two electrodes on a surface of the carrier's body; and
      an identifiable microprocessor capable of handling instructions, wherein the electrodes are coupled to the microprocessor and positioned about the microprocessor; and
   electrically coupling each effector to the conductors through an opening defined in the surface of the carrier's body.

2. A method as in claim 1, wherein each effector comprises:
   at least one sensor coupled to the microprocessor; and
   at least one actuator coupled to the mircropocessor.

3. A method for configuring a medical carrier of the type including a plurality of satellite units, wherein the method comprises:
   positioning at least two separately identifiable effectors along an elongate body, wherein each effector comprises:
      a microprocessor capable of handling instructions; and
      a plurality of electrodes that are positioned about the microprocessor and electrically coupled to the microprocessor and controlled thereby;
   electrically coupling the microprocessor of each effector to a pair of shared conductors running the length of the elongated body, wherein the shared conductors carry power and data; and
   configuring each effector through instructions provided to its corresponding microprocessor using one conductor of the pair of shared conductors.

* * * * *